(12) United States Patent
Gobet et al.

(10) Patent No.: US 7,270,736 B2
(45) Date of Patent: Sep. 18, 2007

(54) ELECTRODE SYSTEM FOR ELECTROCHEMICAL SENSOR

(75) Inventors: Jean Gobet, Corcelles (CH); Philippe Rychen, Muespach-le-Haut (FR)

(73) Assignee: Adamant Technologies SA, La Chaux-de-Fonds (CH)

( * ) Notice: Subject to any disclaimer, the term of this patent is extended or adjusted under 35 U.S.C. 154(b) by 298 days.

(21) Appl. No.: 10/478,749

(22) PCT Filed: May 16, 2002

(86) PCT No.: PCT/CH02/00269

§ 371 (c)(1),
(2), (4) Date: Nov. 24, 2003

(87) PCT Pub. No.: WO02/095387

PCT Pub. Date: Nov. 28, 2002

(65) Prior Publication Data

US 2004/0154934 A1    Aug. 12, 2004

(30) Foreign Application Priority Data

May 22, 2001    (CH) ..................... 0950/01

(51) Int. Cl.
*G01N 27/333*    (2006.01)
(52) U.S. Cl. ................. 205/787.5; 205/778.5
(58) Field of Classification Search ............. 204/402, 204/433, 280; 205/335, 459, 778.5, 787.5
See application file for complete search history.

(56) References Cited

U.S. PATENT DOCUMENTS 4,062,750 A * 12/1977 Butler ..................... 257/253
5,512,489 A    4/1996 Girault et al. ............ 205/777.5
5,597,463 A    1/1997 Birch et al. ............. 204/405
6,020,110 A    2/2000 Williams et al. ........... 430/315
6,051,380 A * 4/2000 Sosnowski et al. ........... 435/6

FOREIGN PATENT DOCUMENTS

| DE | 41 31 731 | 5/1993 |
| DE | 4131731 A1 * | 5/1993 |
| FR | 2 675 260 | 10/1992 |
| GB | 2290617 | 1/1996 |
| WO | WO97/38301 | 10/1997 |

OTHER PUBLICATIONS

Ross, B et al., "Ultramicroelectrode arrays as transducers for new amperometric oxygen sensors," 1992, Sensors and Actuators B, vol. 7, pp. 758-762.*

Ross, B. "Ultramicroelectrode Arrays As Transducers For New Amperometric Oxygen Sensors" *Sensors and Actuators B*, B07:1/3: 758-762; Mar. 1, 1992.

* cited by examiner

*Primary Examiner*—Alex Noguerola
(74) *Attorney, Agent, or Firm*—Townsend M. Belser, Jr.; Nexsen Pruet Adams Kleemeier, LLC

(57) ABSTRACT

The system concerns an electrode system for an electrochemical sensor, comprising, arranged on a conductive substrate (10), a plurality of micro-discs (22) electrically connected to the substrate and a generating electrode (20) insulated from the substrate by an insulating layer (14) and including a plurality of orifices (24) concentric with said micro-discs. A conductive layer (12) and connections (26, 28) enable to connect the electrodes to power sources. The generating electrode enables to modify locally, at the micro-discs, the concentrations of species present in solution opposite said electrodes.

10 Claims, 3 Drawing Sheets

ELECTRODE SYSTEM FOR ELECTROCHEMICAL SENSOR

The present invention relates to electrochemical sensors for measuring the concentration of a chemical substance in a liquid. Such devices find particularly advantageous, but not exclusive, application in the detection of chlorine levels in drinking water or swimming pool water.

Electrochemical sensors of this type necessarily include an indicating electrode, a reference electrode and a counter-electrode. Another type of such sensors is also known, including, in addition, a so-called generator electrode and its counter-electrode. The addition of these last two electrodes, whose effect is to create modifications in the concentration of species present in solution, allows the environment of the indicating electrode to be monitored locally. For example, the pH of the solution can be modified locally by applying a current to the generator electrode. A cathode current will cause the production of OH− ions (the pH then becoming more basic) and, conversely, an anode current will cause the production of H+ ions (the pH then becoming more acidic). A counter-electrode associated with the generator electrode, a counter-electrode associated with the indicating (or working) electrode and a reference electrode are necessary to make a complete sensor. These latter electrodes, whose dimensions do not need to be microscopic, are well known in the field concerned and can be separately mounted. U.S. Pat. No. 5,597,463 discloses, for example, a sensor of this second type, intended for carrying out titration, and with which the measurement carried out is of the potentiostatic type.

It will be readily understood that it is particularly advantageous to use, as an indicating electrode, electrodes of very small dimensions, not only because this allows the space between the indicating electrode and the generator electrode to be reduced, but also because the effects of the liquid turbulence in the cell are minimized.

GB Patent No. 2 290 617 proposes a micro-electrode structure wherein the indicating electrode and the generator electrode take the form of two comb-like structures with interdigitated fingers. For at least one of the combs, the width of the fingers is less than 25 µm whereas their length is 20 or more times greater than the width. Typically, the length of these fingers is several millimeters and the width is 20 µm, the space between two adjacent fingers of the two combs being able to be 20 µm.

It is an object of the present invention to provide an electrode system wherein the indicating electrode and the generator electrode also have micro-structures but whose efficiency is improved and production cost is reduced, with respect to existing embodiments.

More precisely, in order to achieve this object, the invention concerns an electrode system for an electrochemical cell, of the type including a substrate and, arranged thereon, close to each other, an indicating electrode and a generator electrode. This system is characterized in that:
the indicating electrode is formed of a plurality of electrically conductive micro-discs regularly distributed over the substrate and electrically connected to each other; and
the generator electrode is formed of an electrically conductive plate pierced with circular orifices of greater diameter than that of the micro-discs and arranged such that each orifice is concentric with a micro-disc.

Advantageously, the micro-discs have a diameter of approximately 5 to 20 µm and are spaced at a distance of approximately 100 to 400 µm from each other, whereas the orifices have a diameter approximately 10 to 100 µm greater than the diameter of the micro-discs.

According to a preferred embodiment:
the substrate is electrically conductive;
an electrically insulating layer is deposited on the substrate and pierced with a plurality of circular orifices;
the micro-discs forming the indicating electrode are formed of a conductive layer deposited in these orifices in contact with the substrate; and
the generator electrode is formed by a conductive layer deposited on the insulating layer.

In this first embodiment, the substrate is advantageously made of silicon made conductive by doping and an electrically conductive layer is deposited thereunder.

According to a second preferred embodiment:
the indicating electrode is formed by a conductive layer deposited on the substrate;
an electrically insulating layer is deposited on the conductive layer and pierced with a plurality of circular orifices delimiting the micro-discs of the indicating electrode; and
the generator electrode is formed by a conductive layer deposited on the insulating layer.

In this second embodiment, the substrate can either be made of glass or quartz, or of silicon coated with an insulating layer, or silicon made conductive by doping, with, then, an electrically conductive layer deposited thereunder.

It is another object of the present invention to provide a method for determining the pH of chlorinated water using the sensor with the aforecited features.

Other features of the invention will appear from the following description, made with reference to the annexed drawing, in which.

Figure 1:
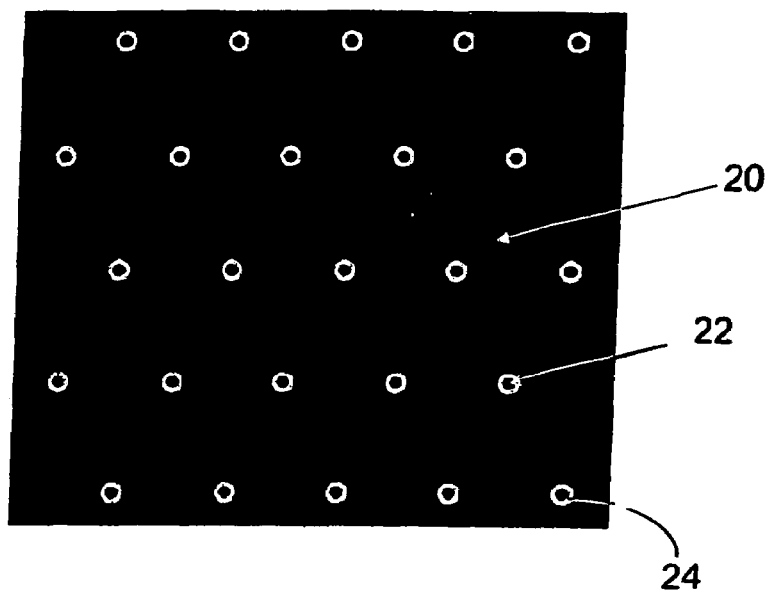
FIG. 1 is a plan view of a micro-electrode system according to the invention.
Figure 2:
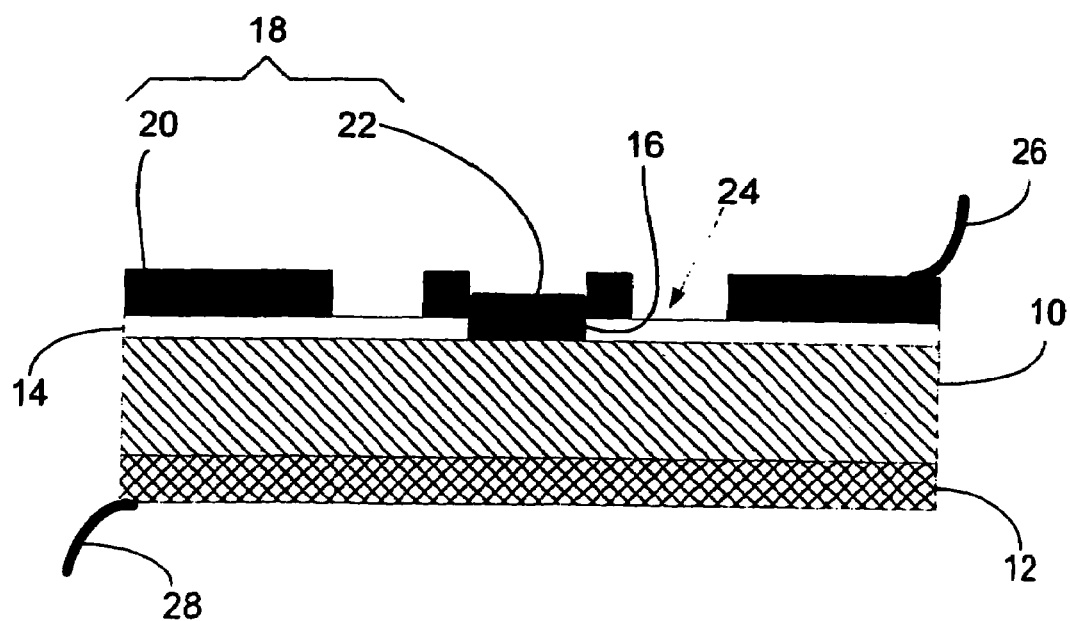
FIG. 2 is a large scale partial cross-sectional view of a first embodiment of the system of FIG. 1.

Reference will be made first of all to FIGS. 1 and 2, which show at 10 an electrically conductive substrate, which takes the form of a square plate with, typically, sides of 2 to 10 mm and 0.5 mm thick. This plate is, advantageously, made of silicon made conductive by doping in accordance with techniques well known to those skilled in the art.

The bottom face of substrate 10 is coated with a conductive layer 12 made, for example, of titanium or aluminium or formed of a stack of three sub-layers of titanium, platinum or gold. The thickness of this layer, deposited in accordance with any known metallization process, is approximately 0.2 to 0.3 µm.

In a variant, substrate 10 can be a simple metal plate. In such case, conductive layer 12 is omitted.

The top face of substrate 10 is coated with an insulating layer 14 formed, for example, of a stack of two sub-layers of $SiO_2$ and $Si_3N_4$ known to have excellent stability in an aqueous medium. The thickness of this layer is around 0.1 to 0.2 µm.

Insulating layer 14 is pierced, for example by etching in a fluorinated plasma, with a regular network of circular through orifices 16, typically having a diameter of approximately 2 to 20 µm and spaced from each other at a distance of approximately 100 to 400 µm. In the example shown in FIG. 1, the spacing is 300 µm.

The top face of insulating layer 14, and orifices 16 made therein, are coated with a conductive layer 18 bearing the reference 20 when it is on layer 14 and the reference 22 when it forms a micro-disc resting in one of circular orifices 16. This layer 18 is formed, for example, of a stack of an adhesion layer, a diffusion barrier layer and a layer of the desired electrode material. This stack, for example, of titanium, platinum and gold, is deposited in a single operation, in accordance with any known metallization method, and has a single thickness of around 0.2 to 0.3 µm.

Layer 18 deposited on insulating layer 14 is pierced, by chemical etching, plasma etching or in accordance with the so-called "lift-off" method, with a network of annular orifices 24 each surrounding one of micro-discs 22 and having an external diameter of around 30 to 120 µm. The typical width of annular space thereby released around the micro-discs is 5 to 50 µm. It will be noted that layer 18 is etched such that micro-discs 22 have a slightly greater diameter than that of orifices 16, for the purpose of preventing any contact between the solution to be measured and substrate 10.

Thus, a microstructure is made for an electrochemical sensor, wherein:

conductive layer 20 forms the generator electrode which can be directly connected to an energy source by a connection 26, and the set of conductive micro-discs 22 form the indicating electrode that can be connected to the energy source through substrate 10 and layer 12, both conductors, by a connection 28 connected to the latter.

Figure 3:
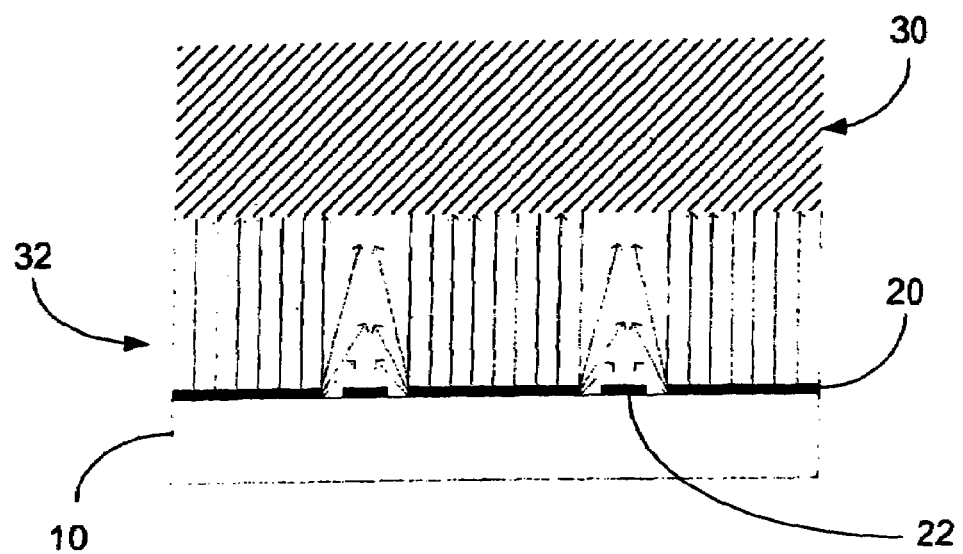
FIG. 3 is a diagram showing the effect obtained by such an electrode system.

As already mentioned, the effect of generator electrode 22 is to create, in its proximity, $H^+$ or $OH^-$ ions depending on the polarizations applied. FIG. 3 shows schematically that, in liquid 30 into which the structure according to the invention is plunged, this electrode establishes a diffusion zone 32 typically having a thickness of 50 to 500 µm depending on the hydrodynamic conditions, and in which the ions created have a concentration gradient. The environment of indicating electrode 22 could thus be modified (increase or decrease in pH) so as to be optimum for the analysis of the detected species. These ions then react with the substances sought in the liquid and the resulting modifications in the ionic concentration are detected owing to the set of micro-discs 22 forming the indicating electrode.

The structure that has just been described has two types of advantages compared to that of GB Patent No. 2 290 617 (already mentioned). First of all, since the micro-discs have two small dimensions (length and width) with respect to the thickness of the diffusion layer, they are microelectrodes in the strict sense of the term. Conversely, the micro-lines described in the aforecited document only have one micrometric dimension; thus they can only be considered as microelectrodes as regards a single direction of the solution flux. The structure according to the invention has, amongst others, the following advantages. First, it offers better independence as regards the turbulence and direction of the liquid in the measuring cell and, secondly, it has less sensitivity to the conductivity of the liquid and offers a better signal/noise ratio. Finally, it ensures a unique and perfectly symmetrical spacing between the indicating electrode and the generator electrode. The action of the generator electrode is greatly improved because of the fact that it has a larger surface area than that of the micro-discs, which form the indicating electrode, and it is located very close to the latter. Moreover, the proposed structure is compatible with batch manufacturing techniques and, according to one of its variants, enables electrical connection through the back face of the indicating electrode.

Figure 4:
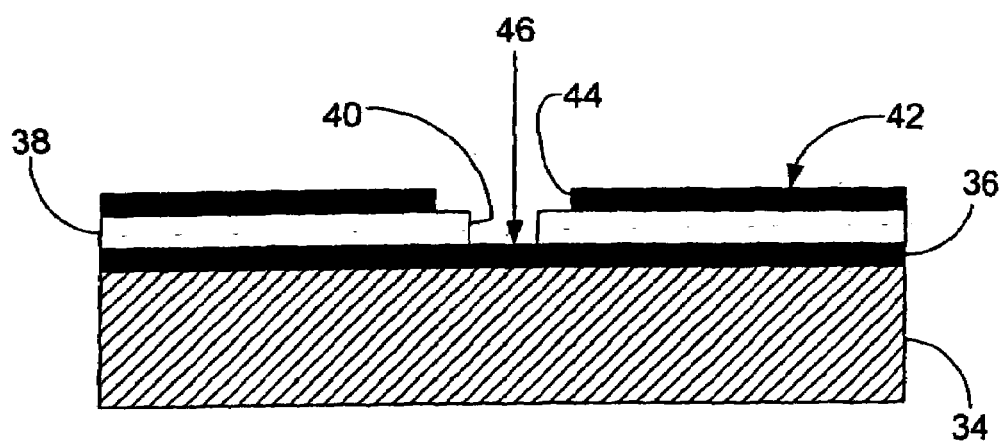
FIG. 4 is a large scale partial cross-sectional view of a second embodiment of the system of FIG. 1.

Reference will now be made to FIG. 4, which shows an alternative embodiment of the structure described hereinbefore. In this case, the conductive substrate 10 of FIG. 2 is replaced by an insulating substrate 34, for example, made of glass or quartz.

The top face of substrate 34 is coated with a conductive layer 36, which, like layer 18, is made, for example, of titanium or formed of a stack of three sub-layers of titanium, platinum and gold. It is deposited in accordance with any known metallization process and has a thickness of approximately 0.2 to 0.3 µm.

The top face of conductive layer 36 is coated with an insulating layer 38, which, like layer 14, is formed, for example, of a layer of non stoichiometric silicon nitride (SiNx), which can be deposited using a low temperature method (PECVD). The thickness of this layer is typically around 0.1 to 0.2 µm. In order to obtain better stability in an aqueous medium, a photosensitive organic polymer, of the epoxy or polyimide type, with a typical thickness of 1 to 2 µm can also be used instead of silicon nitride.

Insulating layer 38 is pierced, by chemical etching, with a regular network of through circular orifices 40 typically having, like orifices 16, a diameter of around 2 to 20 µm and spaced at a distance of around 300 µm.

The top face of insulating layer 38 is coated with a conductive layer 42 of the same composition and thickness as layer 36. This layer 42 is pierced, by chemical etching, with a network of circular orifices 44 each surrounding one of orifices 40 of layer 38. The annular space thereby freed around orifices 40 is typically of 5 to 50 µm.

Thus, according to this first variant, a microstructure for an electrochemical sensor is made, wherein:

conductive layer 42 forms the generator electrode which can be directly connected to an energy source by a connection that is not shown, and conductive layer 36 forms the indicating electrode, active only via its portions 46 uncovered by orifices 40, which can be directly connected to the energy source by a connection that is not shown.

The alternative embodiment of FIG. 4 can, itself, give rise to a first variant wherein substrate 34 is formed of a silicon plate that is not specially doped, coated with an insulating layer and to a second variant wherein the substrate is formed, as in FIG. 2, of a highly doped silicon plate whose back face is coated with a conductive layer allowing the connection.

Figure 5:
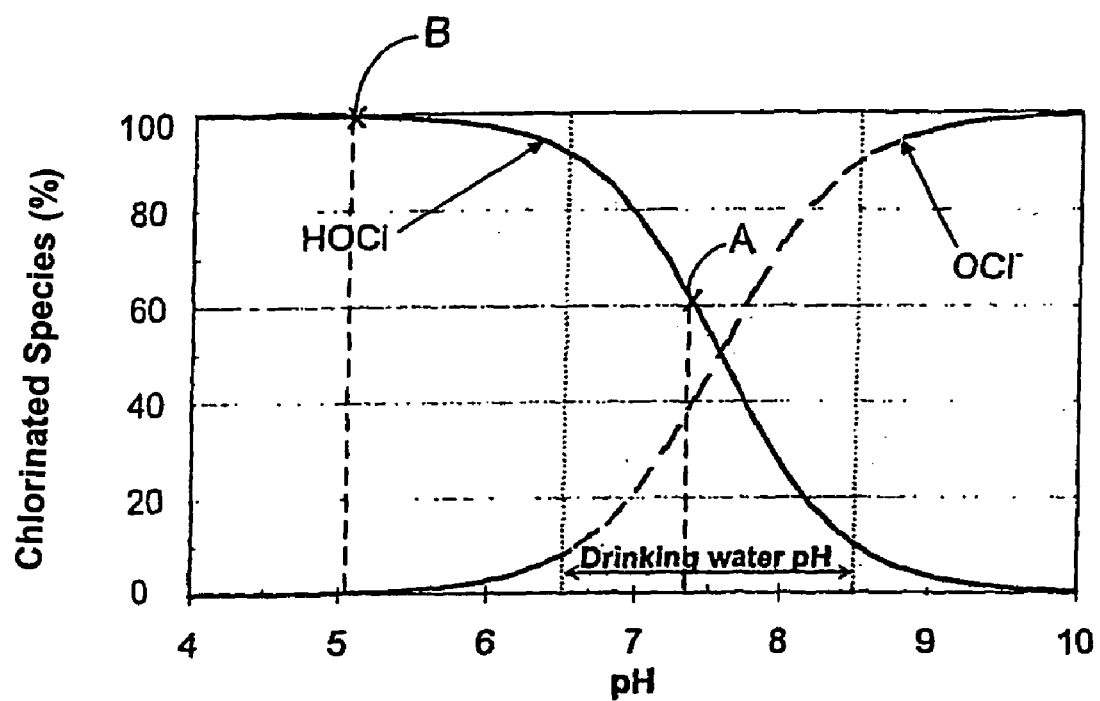
FIG. 5 shows the variation in the chlorinated species in the water as a function of its pH value.

Reference will now be made to FIG. 5 to describe an advantageous application of a sensor provided with a generator electrode according to the present invention. As already mentioned, chlorine is widely used for disinfecting water in swimming pools or drinking water distribution systems. The chlorine added to the water is in the form of hypochlorous acid (HOCl) or in the form of hypochlorite ($OCl^-$), their respective concentrations depending upon the pH value, as indicated by the curves in FIG. 5.

It can be seen in FIG. 5 that the variation in the concentration of hypochlorous acid is at a maximum when the pH varies between 6.5 and 8.5, whereas this same variation is very small when the pH is, either less than 6, or greater than 9. Thus, within the scope of an application of the sensor described hereinbefore in drinking water or swimming pool water containing chlorine, it is possible to measure the pH value of the water by proceeding as follows.

Since the generator electrode is inactive, the concentration A of hypochlorous acid is measured first of all. Next, the generator electrode is activated so as to modify the solution, locally at the micro-discs, by making it more acidic (pH<5.5) and the concentration B of hypochlorous acid is measured. The pH of the solution is then determined by the value of the A/B ratio. In order for this determination to be as precise as possible, the following precautions should, however, be taken. The material forming the indicating electrode will have to be very sensitive to hypochlorous acid and very insensitive to hypochlorite. A material, such as carbon, can, in this respect, be considered satisfactory. The use of an anionic membrane, for example made of a material marketed under the name of Nafion, which does not allow anions to pass through (such as OCl⁻ anions) ensures that only the hypochlorous acid will be taken into account. Finally, since the pH of a solution varies with temperature, one will have to ensure that the temperature is the same as that for which the sensor used was calibrated.

The invention claimed is:

1. A method for determining the pH value of chlorinated water using an electrochemical sensor provided with an electrode system for an electrochemical cell comprising:
   an electrically conductive substrate (10);
   an electrically insulating layer (14) deposited on the substrate and pierced with a plurality of circular orifices (16);
   an electrically conductive layer (22) deposited in said orifices (16) in contact with the substrate and on a portion of the insulating layer (10) that surrounds them, forming a plurality of micro-discs, which form an indicating electrode; and
   an electrically conductive layer (20) deposited on the insulating layer (14), pierced with circular orifices (24) of larger diameter than that of the micro-discs and arranged such that each orifice (24) is concentric with a micro-disc, said layer forming a generator electrode; characterized in that it consists in:
   measuring a first concentration A of hypochlorous acid when the generator electrode is inactive;
   activating said generator electrode so as to bring the pH value of the water at the micro-discs of the indicating electrode to a sufficient level of acidity;
   measuring a second concentration B of hypochlorous acid in an acid medium; and
   determining the pH value from the ratio of said first concentration to said second concentration.

2. A method according to claim 1, characterized in that said micro-discs of the electrode system have a diameter of around 2 to 20 μm and are spaced from each other at a distance of around 100 to 400 μm, and in that said circular orifices (24) have a diameter of around 30 to 120 μm.

3. A method according to claim 1, characterized in that said electrically conductive substrate (10) of the electrode system is made of silicon made conductive by doping.

4. A method according to claim 3, characterized in that said electrode system further comprises an electrically conductive layer (12) deposited under the substrate (10).

5. A method for determining the pH value of chlorinated water using an electrochemical sensor provided with an electrode system for an electrochemical cell comprising:
   an electrically insulating substrate (34);
   an electrically conductive layer (36) deposited on the substrate (34) forming an indicating electrode;
   an electrically insulating layer (38) deposited on the conductive layer (36) and pierced with a plurality of circular orifices (40) delimiting a plurality of micro-discs (46) on the indicating electrode; and
   an electrically conductive layer (42) deposited on the insulating layer (38) pierced with circular orifices (44) of larger diameter than that of the micro-discs and arranged such that each orifice is concentric with a micro-disc, said layer forming a generator electrode; characterized in that it consists in:
   measuring a first concentration A of hypochlorous acid when the generator electrode is inactive;
   activating said generator electrode so as to bring the pH value of the water at the micro-discs of the indicating electrode to a sufficient level of acidity;
   measuring a second concentration B of hypochlorous acid in an acid medium; and
   determining the pH value from the ratio of said first concentration to said second concentration.

6. A method according to claim 5, characterized in that said micro-discs (46) of the electrode system have a diameter of around 2 to 20 μm and are spaced from each other at a distance of around 100 to 400 μm, and in that said circular orifices (44) have a diameter of around 30 to 120 μm.

7. A method according to claim 5, characterized in that said electrically insulating substrate (34) of the electrode system is made of glass or quartz.

8. A method according to claim 5, characterized in that said electrically insulating substrate (34) of the electrode system is made of a silicon plate coated with an insulating layer.

9. A method for determining the pH value of chlorinated water using an electrochemical sensor provided with an electrode system for an electrochemical cell comprising:
   a substrate (34) made of silicon made conductive by doping;
   an electrically conductive layer (36) deposited on the substrate (34) forming an indicating electrode;
   an electrically insulating layer (38) deposited on the conductive layer (36) and pierced with a plurality of circular orifices (40) delimiting the micro-discs (46) on the indicating electrode; and
   an electrically conductive layer (42) deposited on the insulating layer (38) pierced with circular orifices (44) of larger diameter than that of the micro-discs and arranged such that each orifice is concentric with a micro-disc, said layer forming a generator electrode; characterized in that it consists in
   measuring a first concentration A of hypochlorous acid when the generator electrode is inactive;
   activating said generator electrode so as to bring the pH value of the water at the micro-discs of the indicating electrode to a sufficient level of acidity;
   measuring a second concentration B of hypochlorous acid in an acid medium; and
   determining the pH value from the ratio of said first concentration to said second concentration.

10. A method according to claim 9, characterized in that said electrode system further comprises an electrically conductive layer deposited under the substrate (34).

* * * * *